United States Patent [19]

McEntee

[11] 4,127,598
[45] Nov. 28, 1978

[54] PROCESS FOR REMOVING BIPHENYLS FROM CHLOROSILANES

[76] Inventor: Harry R. McEntee, 16 Clemente La., Waterford, N.Y. 12188

[21] Appl. No.: 828,367

[22] Filed: Aug. 29, 1977

Related U.S. Application Data

[63] Continuation-in-part of Ser. No. 770,329, Feb. 22, 1977, abandoned.

[51] Int. Cl.² .................................................. C07F 7/20
[52] U.S. Cl. ........................ 260/448.2 E; 260/448.8 R
[58] Field of Search .................................. 260/448.2 E

[56] References Cited

U.S. PATENT DOCUMENTS 2,972,626   2/1961   Marotta ......................... 260/448.8 R

OTHER PUBLICATIONS

Bernardin, "Results of Field Tests to Determine Effectiveness of Granular Carbon for Removal of Polychlorinated Biphenyls from Industrial Effluent", Calgon Corp.

Primary Examiner—Paul F. Shaver

[57] ABSTRACT

A process for removing impurities such as biphenyls from impure silanes and siloxanes comprising contacting said impure silanes and siloxanes with an adsorbent bed selected from the class consisting of a molecular sieve bed and a charcoal bed such that said impurities are adsorbed on the bed and removing the purified silanes and siloxanes from said adsorbent.

20 Claims, 1 Drawing Figure

Fig. 1.

PROCESS FOR REMOVING BIPHENYLS FROM CHLOROSILANES

BACKGROUND OF THE INVENTION

The present application is a continuation-in-part of parent application Ser. No. 770,329, filed on Feb. 22, 1977, now abandoned.

The present invention relates to the purification of silanes and siloxanes and more particularly the present invention relates to the purification and removal from silanes and siloxanes of biphenyls and chlorinated biphenyls.

Recently it has been postulated that biphenyls and more specifically polychlorinated biphenyls as well as vinyl chloride and carbon tetrachloride might be hazardous to the health of human beings and as such, contact with such materials should be avoided as much as possible.

Accordingly, it has become highly desirable in the chemical industry that chemicals processed in a plant and chemicals transmitted or sold from manufacturing plants contain as small amount of biphenyls and other impurities in them as possible.

In the silicone industry, phenylchorosilanes. are produced by reacting chlorobenzene with silicon metal in the presence of a minor amount of hydrogen chloride gas and a metal copper catalyst at temperatures of about 500° C and above to produce a variety of chlorosilanes. The materials produced by the reaction of the chlorobenzene with silicon metal are hydrotrichlorosilane, silicon tetrachloride, hydrophenyldichlorosilane, phenyltrichlorosilane, and diphenyldichlorosilane. These materials are utilized in the manufacture of various silicon polymers and in the production of various silicone products. Unfortunately, in some cases in such a process for producing such phenylchlorosilanes, there are produced minor amounts of biphenyls and chlorinated biphenyls which it is desirable to remove from the product. Also, impurities such as vinyl chlorides and carbon tetrachloride may accidentally become mixed with streams of silanes and siloxanes. In some instances such separation of the biphenyls and other impurities from the desired chlorosilane product can be accomplished by distillation. However, in the case of one of the important products of the foregoing reaction, that is diphenyldichlorosilane, ordinary ways of separating the biphenyls from the diphenyldichlorosilanes are difficult. For instance, as a result of the fact that the boiling point of diphenyldichlorosilane is within the general proximity to the boiling points of various chlorinated biphenyls, it is difficult to purify the diphenyldichlorosilane and remove from it the biphenyls with ordinary distillation procedures. It should be noted that diphenyldichlorosilane is a highly desirable silane product since it provides one way of incorporating phenyl groups into silicone polymers and which silicone polymers can be utilized to prepare silicone products. In another vein, it is highly desirable to purify diphenyldichlorosilane completely from polychlorinated biphenyls and other impurities so that such chlorosilanes may be utilized to produce a variety of products for the silicone industry.

It should also be noted that in the process of polymerization in a silicone chemical plant, there is also the possibility that biphenyls may be introduced in silicone polymers from external sources, that is, in siloxane polymers as well as in the silanes that are produced intra the manufacturing plant. Sometimes purification can be accomplished by distillation but there are some cases, as was the case with the diphenyldichlorosilane, that because of the proximity of boiling points between the biphenyls and the boiling point of the composition in which it is difficult to separate out the biphenyls by ordinary distillation techniques. Accordingly, it is highly desirable in some cases not only to separate out biphenyls from phenylchlorosilanes that are produced by the process which was explained above, but also to have a purification technique in a manufacturing plant for removing any type of biphenyls and other impurities such as vinyl chloride and carbon tetrachloride from chlorosilanes and siloxanes that may be present.

Accordingly, one way of accomplishing such separation techniques of such biphenyls and other impurities from streams of chlorosilanes, siloxanes or polysiloxanes can be accomplished, for instance, by the use of liquid chromatography. However, such liquid chromatography separation technique is only suitable for laboratory scale separations. In a second instance, as pointed out above, distillation can be utilized as a purification technique for removing unwanted biphenyls and other impurities but this method is only possible when there is a sufficient difference in boiling point between the silanes and siloxanes and the biphenyls.

Accordingly, it is highly desirable to have a purification technique for removing biphenyls and other impurities from silanes or siloxanes which does not depend on differences in boiling points and which is very effective in removing the undesired biphenyls and which technique can be utilized not only in the laboratory but can be scaled up for use in a manufacturing plant. Accordingly, it is one object of the present invention to provide for a process for removing biphenyls and other impurities, such as vinyl chloride and carbon tetrachloride from silanes and siloxanes.

It is an additional object of the present invention to remove biphenyls and their impurities from chlorosilanes in a very efficient manner and in which said process can be utilized and scaled up for a normal plant operation.

It is an additional object of the present invention to provide for a method for removing biphenyls from diphenyldichlorosilane and other chlorosilanes in an efficient manner. It is yet an additional object of the present invention to provide for a method of removing biphenyls from chlorosilanes and siloxanes by utilizing an adsorbent bed of activated carbon or molecular sieves. These and other objects of the present invention are accomplished by means of the disclosure set forth hereinbelow.

SUMMARY OF THE INVENTION

There is provided by the present invention a process for removing biphenyls and other impurities from impure silanes and siloxanes comprising (1) passing impure silanes and siloxanes into contact with an adsorbent bed selected from the class consisting of molecular sieves and charcoal; (2) removing purified silanes and siloxanes from said adsorbent bed while said purified silanes and siloxanes do not exceed the desired purity; (3) containing transmitting of said impure silanes and siloxanes through said adsorbent bed until said adsorbent bed reaches the saturation points with respect to the adsorption of said biphenyls; (4) adding a push hydrocarbon solvent to said adsorbent bed to displace, remove and recover such silanes and siloxanes in said adsorbent bed for further purification; (5) passing a desorbent hydrocarbon solvent through said adsorbent bed to remove said push hydrocarbon solvent, biphenyls which had been adsorbed, and separating the impure silanes and any residual silanes and siloxanes from said solvent for possible further purification; (6) replacing said desorbent hydrocarbon solvent in said adsorbent bed with purified silanes and siloxanes and recovering impure silanes and siloxanes from said desorbent hydrocarbon solvent; (7) recovering said purified silanes and siloxanes from said adsorbent bed and (8) passing once more the impure silanes and siloxanes through said adsorbent bed and recovering purified silanes and siloxanes therefrom.

The summary given above in describing the process of the invention is simply one of the more preferred embodiments within the present invention. It must be understood that the simplest utilization of the invention of the instant case is simply passing an impure stream of chlorosilanes and specifically phenylchlorosilanes or siloxanes, into contact with an adsorbent bed in which the bed is formed from molecular sieves or charcoal and is more preferably formed from activated carbon. After the impure silanes and siloxanes have come into contact with the adsorbent bed for the desired length of time in accordance with the desired purification of the silanes and siloxanes, there are removed from the adsobent bed the purified silanes and siloxanes while the biphenyls have been adsorbed into the surface of the adsorbent particles.

In addition, it should be pointed out that in the more specific conditions of the process of the instant case, set forth in the initial preferred embodiment, it is not necessary that a push hydrocarbon solvent be utilized since it is possible to carry out the process of the instant case for rejuvenating the adsorbent bed and after it has reached the saturation point, by simply passing the adsorbent hydrocarbon solvent through the bed without the use of a push hydrocarbon solvent. The only problem with this approach is that when such an adsorbent solvent replaces the chlorosilanes and siloxanes that were present in the bed at the termination of the passing of the impure chlorosilanes and siloxanes into the bed the use of the adsorbent hydrocarbon solvent increases the amounts of biphenyls and other impurities that are present in the chlorosilanes or siloxanes that are replaced by the adsorbent hydrocarbon solvent. As such the chlorosilanes and siloxanes which are then recovered from the desorbent hydrocarbon solvent are less pure and would need to be purified to a lower biphenyl content by further contact with the adsorbent bed or another adsorbent bed in accordance with the instant invention.

In the same vein, if a purified chloro or siloxane stream does not displace the desorbent hydrocarbon solvent, as set forth in the preferred embodiment of the instant case above, and simply impure silanes and siloxanes are passed into contact with the adsorbent bed so as to force out the desorbent bed solvent for further purification of silanes and siloxanes stream, then the presence of the desorbent hydrocarbon solvent decreases the efficiency of the adsorbent bed and the purified chlorosilane or siloxane stream that comes out of the adsorbent bed is higher in biphenyls. Thus, if it is desired to obtain a silane or siloxane stream which is very low in biphenyl content and their impurities then there is necessitated the replacing of the adsorbent hydrocarbon solvent with a stream of purified silanes and siloxanes.

As mentioned previously, although the present process is desirable for the purification of impure silanes and siloxanes such as, phenylchlorosilanes, and more specifically, diphenyldichlorosilanes, it can be utilized for the purification of any silane or polysiloxane stream as well as other chemical materials that do not interfere with the adsorbent properties of the activated carbon or molecular sieves. Preferably, the process is carried out at ambient temperatures although slightly elevated tempertures do not detract from the efficiency of the process. The preferred push hydrocarbon solvent is isooctane or any of the saturated aliphatic hydrocarbon solvents and the preferred adsorbent hydrocarbon solvents are the aromatic solvents such as, benzene, chlorobenzene, xylene and toluene.

In addition, it should be pointed out that the rate in which the impure silanes and siloxanes are pased through the adsorbent bed depends on the configuration of the adsorbent bed and its capacity and efficiency for adsorption since if the material is pumped through the adsorbent bed too quickly, then the bed will not have time to completely carry out its adsorbent function and if it is pushed through the bed at too slow a rate then the biphenyls diffuse more slowly to the adsorbent due to the less turbulence in the liquid phase.

Generally, anywhere from 5 to 500 pounds of a stream of impure silanes or siloxanes can be pumped per hour, per square foot of cross-section of the adsorbent bed. However, the above ranges are exemplary and the actual pump rate of the impure silane or siloxane stream through the adsorbent bed will depend on the configuration and design of the bed as well as its cross-section and its adsorbent capacity. The above general range is more of a guidance than a limitation in the instant process.

DESCRIPTION OF THE PREFERRED EMBODIMENT

It can be appreciated that while the instant process is preferably used to remove biphenyls and chlorinated biphenyls from impure silanes and siloxanes, it generally can be used to remove other impurities from streams of silanes or siloxanes. Thus, generally the instant process can be used to remove impurities such as vinyl chloride and carbon tetrachloride from streams of silanes and siloxanes. The instant process can also be utilized to remove any aromatic hydrocarbon impurities from streams of silanes and siloxanes. Such other impurities will hereafter be referred to "as other impurities" in the instant case.

The silicone compounds that can be purified by the process of the instant invention comprise silanes and siloxanes. Such silanes may be chloro-substituted silanes and other types of substituted silanes such as, methyltriacetoxysilane. Generally, most silanes can be used in the instant process since they have a viscosity low enough so that they can be processed through the adsorbent bed. Examples of silanes that can be purified by the instant process are, for instance, methyltrichlorosilane, dimethyldichlorosilane, methyltriacetoxysilane, methyltrimethoxysilane, methyltriethoxysilane, etc. As stated previously, most silanes will have a viscosity of a sufficiently low value such that they can be pumped or processed through the adsorbent bed in the first step of the instant process with facility. Generally, the silanes that can be purified by the instant process have the formula, where R stands for monovalent hydrocarbon radicals and halogenated monovalent hydrocarbon radicals, X stands for hydrolyzable radicals such as, chlorine, alkoxy radicals, acetoxy radicals, amine radicals, etc., and where a is a whole number that varies from 1 to 4. In addition to the silanes that can be purified by the instant process, many siloxanes may be also purified by the instant process. Examples of such polysiloxanes that may be purified by the instant process are dimethylpolysiloxanes, diphenylpolysiloxanes, dimethyldiphenylpolysiloxanes, etc. The siloxanes that may be purified by the instant process generally have the formula, where $n$ varies from 1 to 3, and such that in the siloxanes the R to Si ratio varies anywhere from 1.7:2.1. In the foregoing siloxane formula, R stands for any monovalent hydrocarbon radical or halogenated monovalent hydrocarbon radical such as, alkyl radicals, methyl, ethyl, propyl; alkenyl radicals such as, vinyl, allyl, cycloalkyl radicals such as, cyclohexyl, cycloheptyl; mononuclear aryl radicals such as, phenyl, methylphenyl, ethylphenyl, and etc. and halogentated monovalent hydrocarbon radicals as example of which is, of course, 3,3,trifluoropropyl. Generally, any silane and siloxane which does not poison the adsorbent bed and has a sufficient flow viscosity to be processed through the adsorbent bed can be purified by the instant process to remove biphenyls from it. Other siloxanes that may be purified by the instant process are cyclicpolysiloxanes, tetrasiloxanes, pentasiloxanes and etc. An example of cyclic compounds are such as octamethyltetracyclicsiloxanes and octaphenyltetracyclicsiloxanes. Preferably for use in the instant process the silanes and siloxanes that are utilized in the instant process have a viscosity below 100,000 centipoise at 25° C and more preferably a viscosity below 25,000 centipoise at 25° C. More preferably there is utilized in the instant process the purification of phenylchlorosilanes and phenyl-containing polysiloxanes. The adsorbent bed of the instant process can likewise be comprised of a number of different materials and more preferably is selected from charcoal and molecular sieves, the charcoal being more preferred over the molecular sieves since it has a greater adsorbent capacity for biphenyls.

Generally there may be utilized in the adsorbent bed of the instant process any charcoal within the size limitation mentioned below. One type of charcoal that is especially preferred is activated carbon. Activated carbon is preferred since it has a greater adsorbent capacity than ordinary charcoal. Activated carbon is obtained by heating ordinary charcoal to very high temperatures so as to remove volatiles and make it more adsorbent. If the charcoal is utilized, it is preferred that such charcoal have a U.S. mesh size of anywhere from 4,000 mesh to one quarter inch. Examples of materials that can be utilized in the adsorbent bed in the first step of the instant process is activated carbon Pittsburgh BL;325 mesh, manufactured by Calgon Corporation; activated carbon Pittsburgh Cal, 12 × 40 mesh, manufactured by Calgon Corporation; active coconut charcoal Pittsburgh PCB - 4 × 10 mesh, manufactured by Calgon Corporation; coconut charcoal 70 × 80 mesh, sold by Analabs. Inc.; 10 molecular sieves 45 × 60 mesh, Hylar M, manufactured and sold by Guild Corporation, and 13 molecular sieves 600 mesh manufactured and sold by Davison Chemical Division of W. R. Grace and Company. It should be noted that it is preferred that the molecular sieves also have a size of anywhere from U.S. mesh 4000 to one quarter inch in size.

In the first step of the process the impure chlorosilane or siloxane stream is passed through the adsorbent bed containing the foregoing adsorbents as discussed above. Preferably, the adsorbent bed is in a vertical column but it can also be in a horizontal bed. It should be noted that the preferred U.S. mesh size for the molecular sieves and the charcoal or activated carbon can be anywhere from 50 mesh to one eighth inch. Accordingly, the impure silanes and siloxanes are passed through the adsorbent bed until the effluent from the adsorbent bed has reached the level of purity in which it is desired that the purified silanes and siloxanes be with respect to containing biphenyls.

It should be noted that there does not necessarily have to be one bed processing the impure silanes and siloxanes bu there is preferably a number of columns containing a number of adsorbent beds through which the impure silanes and siloxanes are passed in order. Generally, the rate at which the impure silanes and siloxanes will be passed through the adsorbent bed will depend on the viscosity of the silanes or siloxanes and also on the particle size of the activated carbon or molecular sieve in the adsorbent bed. For most purposes, a flow rate of the impure silanes and siloxanes through the adsorbent bed will be monitored to be anywhere from 5 to 500 pounds per hour, per square foot of cross-section of the adsorbent bed. However, the above is just a general range and the actual range that is utilized in accordance with the instant process will depend on the above factors and also on two other factors. If the stream of silanes and siloxanes is passed through the adsorbent bed at too fat a rate then the capacity of the adsorbent bed may be surpassed in the ability of the bed to absorb the biphenyls and their impurities from the silane and siloxane stream. On the other hand, if the flow rate is too slow then the biphenyls adsorb more slowly due to less turbulence in the liquid phase and the bed operates less efficiently.

Accordingly, within the above caveats, the flow rate of the impure silane and siloxane stream through the adsorbent bed will be determined by the above factors. Accordingly in the first step of the instant process, the impure silane and siloxane stream will be forced into contact with the adsorbent bed until the biphenyls and other impurities in the effluent coming from the adsorbent bed has increased to a level that the content of biphenyls that are permitted for a particular product has been reached. At this step of the process, a desorbent solvent may be pushed through the adsorbent bed to desorb the biphenyls from the adsorbent bed and thus rejuvenate the adsorbent bed for adsorbing biphenyls from additional chlorosilanes and siloxanes which may be passed through the adsorbent bed.

In a more preferred modification of the instant process and so as to obtain the maximum use of the adsorbent bed the impure stream of silanes or siloxanes will be continually passed through the adsorbent bed after the purification limit of biphenyls and other impurities has been reached until the adsorbent bed has reached its capacity for adsorbing biphenyls and other impurities, that is, until the adsorbent bed has adsorbed so many biphenyls and other impurities that it is incapable of adsorbing significant quantities of additional biphenyls and other impurities from the impure stream of silanes and siloxanes being processed.

Accordingly, this allows the worker skilled in the art to continue using the bed for the adsorption of biphenyls from an impure stream of silanes and siloxanes after the purification limit for a particular desired level of biphenyls and other impurities from the impure stream of silanes and siloxanes has been reached. Accordingly, in the preferred embodiment of the instant case the adsorbent bed is utilized to continue adsorbing biphenyls from the impure stream of silanes and siloxanes until its adsorption capacity has been reached.

Generally, this means that the adsorbent bed is adsorbing from 5% to 25% by weight or less of the impurities in the feed silane or siloxane stream that is fed to the adsorbent bed. The stream of silanes and siloxanes effluent from the adsorbent bed the adsorbent bed having the higher levels of biphenyls in it in excess of the purification level is collected from the adsorbent bed and can be further processed in other adsorbent beds until enough biphenyls have been removed from it such that it reaches the upper purification level for desired biphenyls of the particular impure silane or siloxane product.

This preferred step of continuing passing the impure silanes and siloxanes to the adsorbent bed after the purification limit has been reached allows the maximum use of the adsorbent bed in the instant process. Accordingly, irrespective of which level has been reached, that is, the purification limit of the impure silanes and siloxanes stream or the adsorbent capacity of the adsorbent bed, it is then necessary to rejuvenate the adsorbent bed for maximum economy in the instant process by removing the biphenyls that were absorbed on the adsorbent bed. Of course, it can be simply stated that the adsorbent bed may simply be discarded and new adsorbent material placed in the bed, however, this alternative unduly increases the cost of the instant process and would be highly expensive except for laboratory or pilot plant operations.

Accordingly, for maximum efficiency and economy in the instant process it is necessary to rejuvenate the adsorbent bed by removing the adsorbed biphenyls and other impurities from the charcoal or molecular sieves. Accordingly, in the most simple utilization of the instant process there can then be pushed a desorbent hydrocarbon solvent through the adsorbent bed such that the solvent desorbs the biphenyls from the surface in the adsorbent bed and thus purifies the adsorbent bed so that it can be reutilized to adsorb biphenyls from an impure stream of silanes and siloxanes. However, in a more preferred embodiment of the instant case, there is utilized a push hydrocarbon solvent first. The push hydrocarbon solvent is one which is relatively weakly adsorbed by the adsorbent. For instance, such an adsorbent solvent may be any aliphatic saturated hydrocarbon solvent such as hexane, heptane, octane, etc., and more preferably, in the instant case, iso-octane. Other examples of preferred push hydrocarbon solvents are, for instance, hexene, acetone, ethyl ether, ethyl acetate.

The function of the push hydrocarbon solvent is to simply displace the silane or siloxane in the adsorbent bed at the termination of the adsorption step of adsorbing the biphenyls from the impure silanes and siloxanes that are being processed. If a push hydrocarbon solvent is not utilized in the less preferred embodiment of the instant case and a desorbent hydrocarbon solvent is immediately utilized, then the desorbent hydrocarbon solvent which has an affinity for biphenyls will attract and impart to the silane and siloxane stream that it displaces in the adsorbent bed a high amount of biphenyls in the displaced amount of silanes and siloxanes which will then have to be purified much more extensively to reach the desired level of purity with respect to biphenyl level than would be the case if a push hydrocarbon solvent is utilized. Accordingly, in the preferred embodiment of the instant case a push hydrocarbon solvent, such as iso-octane, is utilized to displace the silane and siloxane in the adsorbent bed after the adsorbent bed has reached its capacity for adsorbing biphenyls or after the level of purity desired in the purified effluent from the adsorbent bed has been reached. Generally, the amount of such push hydrocarbon solvent will be equal to the volume of the adsorbent bed. After such push hydrocarbon solvent has displaced the silanes and siloxanes in the adsorbent bed, then it is removed from the adsorbent bed and a desorbent hydrocarbon solvent is passed through the adsorbent bed for purpose of rejuvenating the adsorbent bed and removing the adsorbed biphenyls on the bed. It should be noted that after the push hydrocarbon solvent has passed through the bed it is simply taken and distilled to remove the silanes and siloxanes that have been collected and the silanes and siloxanes that are removed or separated from the push hydrocarbon solvent are then processed to a new adsorbent bed or in the same adsorbent bed after it has been rejuvenated until such silanes and siloxanes reach the necessary purification limit that is desired. In the case where the adsorption is stopped at the point where such silanes and siloxanes have reached the desired purification limit such silanes and siloxanes recovered from the push hydrocarbon solvent by distillation in all likelihood will be pure enough to be incorporated into the purified effluent that was collected from the adsorbent bed. At any case whether further purification is desired, will depend on the particular steps being utilized in the instant process.

In the most preferred embodiment of the instant process after the push hydrocarbon solvent has displaced the silane and siloxane in the adsorbent bed, then a desorbent hydrocarbon solvent is utilized to displace the push hydrocarbon solvent from the adsorbent bed. Such desorbent hydrocarbon solvent must have the property of having a stronger adsorbent attraction for the adsorbent than the biphenyls and other impurities have. For this purpose, as a desorbent hydrocarbon solvent, any polar hydrocarbon solvent may generally be utilized as long as it does not poison the adsorbent bed. Examples of adsorbent hydrocarbon solvents that may be utilized in the instant case are, for instance, aromatic hydrocarbon solvents, chlorinated aromatic solvents and chlorinated aliphatic solvents.

The most preferred adsorbent hydrocarbon solvents are, of course, chlorobenzene, toluene and xylene — the most preferred being chlorobenzene. Other adsorbent hydrocarbon solvents that may be utilized in the instant process to rejuvenate the adsorbent bed are, for instance dichlorobenzene, 1,2, dichloroethane methylene chloride, perchloroethylene. Generally, the desorbent hydrocarbon solvent is passed through the adsorbent bed at about the same rate as that when the impure silanes and siloxanes were passed through the adsorbent bed for purification dependent upon the properties of the desorbent hydrocarbon solvent. Accordingly, generally, the adsorbent hydrocarbon solvent is transmitted to the adsorbent bed at a rate of 5 to 500 pounds per hour, per square foot of cross-section of the adsorbent bed. Of course, the amount of desorbent hydrocarbon solvent will depend on the adsorbent capacity of the bed and the amount of adsorbed biphenyl that it has on it. If the adsorbent bed has of course, a large amount of adsorbed biphenyls then the amount of the adsorbent hydrocarbon solvent will be greater.

Generally, again in most instances the two volumes of the adsorbent bed of adsorbent hydrocarbon solvent will be sufficient to rejuvenate the adsorbent bed. It should be noted that the above rates and volumes of adsorbing hydrocarbon solvent which will be needed is exemplary only since the amount of adsorbent hydrocarbon solvent that will rejuvenate the adsorbent bed to the proper stage for a particular purification process will depend on a number of factors such as for instance the purification limit that is desired for the impure stream of silanes and siloxanes that are processed. Generally, the adsorbent hydrocarbon solvent which may for instance be chlorobenzene displaces the push hydrocarbon solvent and remains in contact with the adsorbent bed sufficiently to adsorb most of the biphenyls that are present in the adsorbent bed.

In the next step of the process in a less preferred embodiment of the instant process, the desorbent hydrocarbon solvent may then be removed from the adsorbent bed and there may be passed through the adsorbent bed a stream of impure silanes and siloxanes from which it is desired to further remove biphenyls therefrom. However, it has been found that when such impure silanes and siloxanes are introduced into the adsorbent bed in the wake of the removal of the adsorbent hydrocarbon solvent, then the initial amount of effluent that is obtained from such an adsorbent bed is higher in content in biphenyls. This effect results from the desorbent hydrocarbon solvent interfering with the function of the adsorbent bed and not allowing the adsorbent bed to fully accomplish its adsorbent function. Accordingly, for a more efficient utilization of the adsorbent bed in accordance with the instant case and to minimize the amounts of effluent of silanes and siloxanes from the adsorbent bed that will have to be reprocessed so as to remove biphenyls so that the biphenyl content will reach the desired limit for a particular operation, it is preferred to displace the desorbent hydrocarbon solvent in the adsorbent bed with a purified stream of silanes or siloxanes. The desorbent hydrocarbon solvent is then subjected to distillation procedures until the silane and siloxanes that have been mixed with it in accordance with the instant process can be separated out and subjected to further purification through a rejuvenated adsorbent bed so that such silanes and siloxanes can be purified to the desired content of biphenyls and other impurities.

It should be noted, of course, that the desorbent hydrocarbon solvent and the push hydrocarbon solvent after they have been purified by the distillation procedure can be once again used in the instant process for in the case of the push hydrocarbon solvent for displacing the silanes and siloxanes in the adsorbent bed and in the case of the desorption hydrocarbon solvent for being utilized to rejuvenate an adsorbent bed by removing the biphenyls therefrom. Accordingly, in the more preferred embodiment of the instant case a purified stream of silanes and siloxanes are utilized to displace the desorbent hydrocarbon solvent from the adsorbent bed which desorbent hydrocarbon solvent is then collected and purified with a recovery of any silanes or siloxanes in it by such procedures as distillation. When the desorbent hydrocarbon solvent has been completely replaced by the purified silane and siloxanes in the adsorbent bed then the stream of silanes and siloxanes that is desired to be purified further is reprocessed through the adsorbent bed.

Accordingly, with the use of purified silanes or siloxanes to displace the adsorbent hydrocarbon solvent there results an effluent from the adsorbent beds column that is very low in content of biphenyls and allows the adsorbent bed to remove biphenyls such that the biphenyl content in the effluent from the adsorbent bed reaches a level of parts per billion. At this point the process is simply repeated, the stream of silanes and siloxanes are processed through the adsorbent bed until the level of purity in the effluent from the adsorbent bed has reached the desired level in which case the purified product is collected as such. Then preferably, the adsorbent bed can continue to adsorb biphenyls and other impurities from the stream of silanes and siloxanes until it has reached its adsorption capacity as explained above. In any case the purified stream of silanes and siloxanes that was initially utilized to displace the desorbent hydrocarbon solvent from the adsorbent bed can always be collected as purified product because its content of biphenyls remains at about the level which that it was prior to its introduction to the adsorbent bed to displace the desorbent hydrocarbon solvent. In any case the process is re-repeated in accordance with the steps set forth above to continue removing biphenyls from a stream of silanes and siloxanes until the silanes and siloxanes are purified to the desired level of biphenyl content. It should be noted that with the instant process an impure stream of silanes and siloxanes can be purified until it has the desired level of biphenyls in it down to a level of parts per billion of biphenyl content. It should also be noted that the biphenyls contacted in the push hydrocarbon solvent and in the desorbent hydrocarbon solvent, such biphenyls can simply be removed by distillation from the solvents and burned and thus destroyed. In a simpler but not as economical procedure, the desorbent hydrocarbon solvent stream and the push hydrocarbon solvent stream with any biphenyls present after the silanes and siloxanes have been separated from them may simply be destroyed by burning along with the biphenyls in them. Also, it is highly desirable that most silanes and siloxanes that are present in the push hydrocarbon solvent and in the desorbent hydrocarbon solvent be removed and further purified so as to increase the yield and minimize the losses in the impure silane and siloxane stream that is to be purified and reduced in biphenyl content.

It will also be appreciated that the simplest embodiment of the instant process comprises passes the impure stream of silanes and siloxanes through an adsorbent bed as described above. In a more involved ramification of the instant process, if it is not decided to discard the used adsorbent bed and to rejuvenate it then a desorbent hydrocarbon solvent may be utilized for such a purpose as described as above. The most preferred embodiment of the instant process is utilized when it is desired to purify the stream of silanes and siloxanes to the desired level and minimize losses of product and for economic utilization of the adsorbent bed. Then in those uses the above preferred embodiment of the instant invention should be utilized in all its aspects, such as the use of the push hydrocarbon solvent and also the use of the purified stream of silanes and siloxanes to displace the desorbent hydrocarbon solvent as was explained above. Naturally as can be expected the different steps of the instant process, depending on a particular need for removing of biphenyls from silanes and siloxanes, may be subjected to modification in addition to what has been described above. Thus, instead of a push hydrocarbon solvent there may be utilized an inert gas such as nitrogen to displace the silanes and siloxanes in the adsorbent bed after the adsorbent bed has reached its adsorption capacity. Further, in place of the desorption hydrocarbon solvent the bed having an atmosphere of nitrogen in it can be simply heated to temperatures above 100° C and with a stream of nitrogen passing through the bed so as to vaporize and remove the biphenyls with such stream of nitrogen or other inert gas, that does not poison the adsorbent bed. Although a push inert gas in place of the push hydrocarbon solvent has many advantages such as a simplicity in separating the silanes and siloxanes from the gas, the heating of the adsorbent bed is not as advantageous since this is not a very economical way to rejuvenate the adsorbent bed; that is to have heating facilities or heating jackets on the bed sufficient to heat the adsorbent bed to the proper level. However, if it is desired to utilize the heated column and to use an inert gas to remove the biphenyls from the adsorbent bed such can be done by passing an inert gas such as nitrogen through the adsorbent bed and the bed can be rejuvenated in that manner. The inert gas with the biphenyls in it can then be processed to remove the biphenyls from it by passing the inert gas to a combustion atmosphere in which the biphenyls will be burned and destroyed. The use of the push hydrocarbon solvent and the desorbent hydrocarbon solvent in the instant process can be carried out at ambient temperatures and as such is simpler to operate than in the case when the inert gas and heating is utilized to rejuvenate the adsorbent bed. Of course, with the alternate process of utilizing nitrogen gas it is much simpler to separate the silanes and siloxanes that are in the adsorbent bed and thus the recovery is maximized than in the case of the push hydrocarbon solvent and adsorbent hydrocarbon solvent.

It should be noted that while the above process has been described above with reference to the removal of biphenyls from silanes and siloxanes that the same process both as to the general as well as the specific embodiments described above can be utilized to remove any of the other impurities described previously (vinyl chloride, carbon tetrachloride, etc).

An exemplary schematic diagram of the instant process to be found in FIG. 1 which discloses a schematic diagram of the utilization of the most preferred embodiment of the instant invention.

Figure 1:
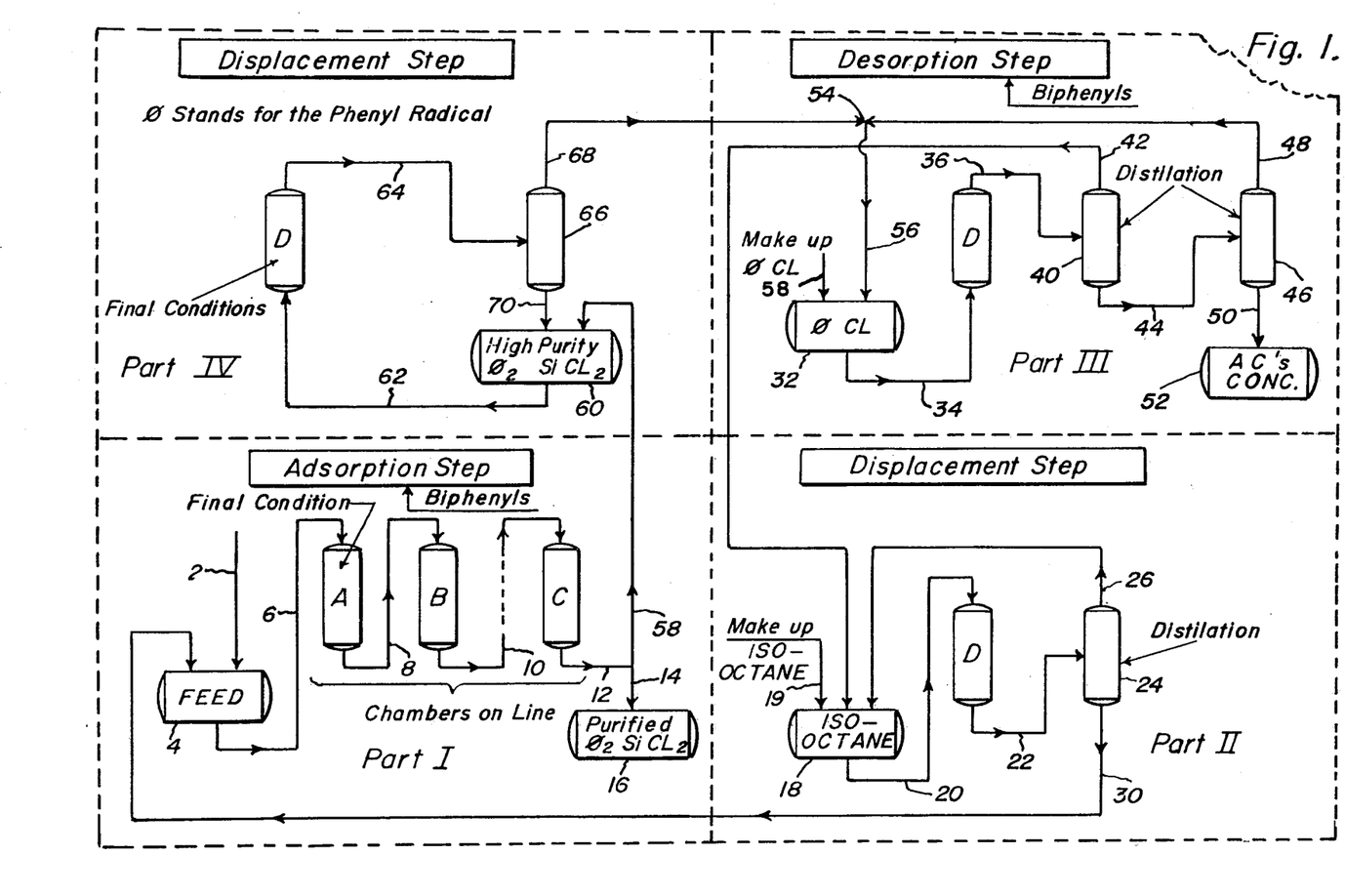

In Part I of FIG. 1, line 2 shows the introduction of an impure stream of silane into the feed tank 4. From feed tank 4 through line 6 there is passed the impure stream of silanes and siloxanes from which there is to be removed biphenyls to adsorbent Columns A, B, & C connected in series by lines 6, 8, and 10. The adsorbent beds are filled with activated carbon.

Finally, the effluent stream emerges from Column C through line 12, then passes into line 14 to purified product tank 16. During such a process which is continuous Column D is shown in Part II of FIG. 1. Column D has reached its maximum point of adsorption and is thus taken off the adsorption stream of removing silanes and siloxanes from feed tank 4 through lines 6, 8 and 10. Accordingly, the silanes and siloxanes in Column D are displaced by the push hydrocarbon solvent iso-octane from tank 18. Iso-octane passes through line 20 to displace the silanes and siloxanes in Column D and the effluent in Column D passes through line 22 into distillation Column 24. In distillation Column 24 the iso-octane is purified and passed back through line 26 to the feed tank of iso-octane that is tank 18. The chlorosilanes that are removed during such distillation in distillation Column 24 are then passed through line 30 into feed tank 4 for further purification.

Column D is then processed through the desorption of the biphenyls in the adsorbent bed of Column D as shown in Part III of FIG. 1. Accordingly, chlorobenzene, a desorbent hydrocarbon solvent, is passed from tank 32 through line 34 in Column D to remove and displace the iso-octane therein and to desorb biphenyls adsorbed on the adsorbent bed.

Accordingly, the chlorobenzene effluent from Column D during this adsorption of biphenyl step is passed through line 36 to distillation Column 40 to purify and remove from distillation Column 40 purified iso-octane which passes through line 42 into iso-octane feed tank 18. It should be noted that new iso-octane is also fed into iso-octane feed tank 18 through line 19 as needed. With respect to Part III of FIG. 1, and with respect to distillation Column 40, the stream of chlorobenzene having chlorosilanes in it and biphenyls is passed from distillation Column 40 through line 44 into distillation Column 46 in which it is further purified to remove an overhead stream containing chlorobenzene and iso-octane, the push hydrocarbon solvent, as well a a minor amount of recovered chlorosilane residue from distillation Column 46, through line 48, valve 54 and line 56 in feed tank 32. A small amount of chlorosilane residue and a high concentration of biphenyls is then passed through line 50 into collection tank 52, where it is subsequently destroyed. There also may be utilized further processes to remove chlorosilanes from the contents of tank 52 before the contents are destroyed by combustion. The overhead stream from Distillation Column 46 passes through line 48 and through valve 54 and line 56 back into the chlorobenzene feed tank 32. If additional chlorobenzene is needed, it can be added to feed tank 32, through line 58.

Adsorption bed Column D is then subjected to the displacement of the chlorobenzene desorbent hydrocarbon solvent with purified chlorosilanes as shown in Part IV of FIG. 1. Purified chlorosilane product is passed from tank 16 in Part I through lines 14 and 58 into high purity chlorosilane tank 60. From tank 60, the purified chlorosilane is passed through line 62 into tank D to displace the chlorobenzene in the adsorbent bed in Column D. From Column D, the chlorobenzene and purified chlorosilanes are passed through overhead line 64 to distillation column 66. In distillation Column 66 the chlorobenzene desorbent hydrocarbon solvent is distilled overhead and passes through line 68, valve 54 and line 56 back into the chlorobenzene feed tank 32. The purified stream of chlorosilane product, as purified or separated from the chlorobenzene in distillation Column 66, then passes through line 70 into high purity chlorosilane feed tank 60, where it is kept for further use in the rejuvenation process of the adsorbent bed columns. At this point, Column D may now be reinserted into the adsorbent bed for adsorption of the biphenyls from the impure stream of chlorosilanes coming from tank 4, as shown in part I of FIG. 1, and another column may be taken out if it has reached its adsorption capacity and subjected to the rejuvenation procedures of Parts II, III and IV as explained above, of FIG. 1.

By the above explained procedure and as forth in the schematic diagram of FIG. 1, under the most preferred embodiment of the instant case there is a continuous process for the adsorbing of biphenyls from an impure stream of silanes and/or siloxanes as may be desired. It should be noted that the schematic diagram of FIG. 1, and as explained above, contains only one preferred embodiment in which the instant process may be utilized in a continuous manner. It should be noted that there may be any modifications to this process than as set forth in the drawing and as is desired and that the instant process can be continuous or may be batch in which the impure stream of silanes and siloxanes are passed through a single column or a number of columns and the columns may be simply shutdown for rejuvenation instead of utilizing the steps set forth in the embodiment of FIG. 1. Such modifications of the process of FIG. 1 or of any of the steps of the instant process will not be explained in detail since such modifications are obvious to a worker skilled in the art. Suffice it to state that the process of the instant case may be modified as is desired to meet a particular need or to be utilized in a manner that produces the most efficiency in a particular purification situation of specific silanes and siloxanes. Although the schematic diagram of FIG. 1 shows a specific procedural set-up for chlorosilanes it may be utilized with well known modifications for the purification of siloxanes. It should be noted that the instant process with the above limitations and having an adsorbent bed to adsorb biphenyls from a stream of silanes and siloxanes may be modified in any way or manner to accomplish a specific purpose or meet a suitable need in the removal of biphenyls from streams of silanes or siloxanes.

The examples below are given for the purpose of illustrating the reduction to practice of the instant case. They are not given for any reason or purpose to limit the definition and scope of the instant invention. In the examples and in the disclosure above, the concentration of the biphenyls in the chlorosilane stream was determined as follows. A weighted portion of the chlorosilane effluent was taken and it was contacted with aqueous potassium hydroxide and hexane. The potassium hydroxide reacted with the chlorosilane and specifically the diphenyldichlorosilane so as to retain it in the aqueous phase and the biphenyls to migrate to the hexane phase. The hexane was then taken and separated and concentrated by stripping so as to concentrate the biphenyls. The hexane stream was then passed through gas chromatography to detect the amount of biphenyls in the initial sample in parts per billion. This method was used throughout the instant examples for measuring the concentration of biphenyls, either in the feed stream or in any of the samples from the product effluent streams as set forth in the examples. It should be noted that while the examples below describe the removal of biphenyls from diphenyldichlorosilanes, the same procedures can be used to remove biphenyls and the other impurities from any stream of silanes or siloxanes.

EXAMPLE 1

To a vessel constructed of a 16 inch schedule 40 steel, ten feet long pipe, filled with 322 lbs. of dry adsorbent (activated carbon, type Pittsburgh CAL, 12 × 40 mesh, manufactured by Calgon Corp.) impure diphenyldichlorosilane ($\phi_2SiCl_2$) containing 2060 PPM of biphenyls was pumped at a mass velocity of 175 lbs. per hour per square foot of vessel cross sectional area and the concentration of biphenyls in the stream as it left the vessel monitored with the following results:

| Lbs. of Effluent $\phi_2SiCl_2$ per lb of absorbent in bed | PPM of Biphenyls in Total Effluent $\phi_2SiCl_2$ |
|---|---|
| 0.81 | 2 |
| 2.44 | 8 |
| 4.09 | 29 |
| 5.80 | 67 |
| 7.41 | 111 |
| 8.46 | 134 |

EXAMPLE 2

At the completion of Example 1, a total of 3630 lbs. of chlorobenzene was passed through the same bed of adsorbent to desorb the biphenyls and regenerate the bed. Impure $\phi_2SiCl_2$ containing 1960 PPM of biphenyls was then passed through the bed at the same mass velocity used in Example 1 and the concentration of biphenyls in the effluent leaving the vessel monitored with the following results:

| Lbs. of Effluent $\phi_2SiCl_2$ per lb of absorbent in bed | PPM of Biphenyls in Total Effluent $\phi_2SiCl_2$ |
|---|---|
| 0.57 | 10 |
| 1.98 | 12 |
| 3.62 | 36 |
| 5.12 | 59 |
| 6.65 | 95 |
| 8.26 | 128 |
| 9.89 | 205 |
| 11.6 | 289 |
| 13.1 | 339 |
| 14.0 | 356 |

EXAMPLE 3

At the completion of Example 2, the same bed was regenerated by passing chlorobenzene through bed, and then impure $\phi_2SiCl_2$ containing 2780 PPM of biphenyls fed through the bed at the same mass velocity used in Example 1, and as before the concentration of biphenyls in the effluent leaving the vessel monitored with the following results:

| Lbs. of Effluent $\phi_2SiCl_2$ per lb of adsorbent in bed | PPM of Biphenyls in Total Effluent $\phi_2SiCl_2$ |
|---|---|
| 0.19 | 20 |
| 1.19 | 15 |
| 2.84 | 18 |
| 4.49 | 36 |
| 6.13 | 61 |
| 7.82 | 113 |
| 9.55 | 161 |
| 11.24 | 218 |
| 12.90 | 268 |
| 14.40 | 327 |
| 15.75 | 422 |
| 16.84 | 500 |

EXAMPLE 4

To the bed used in the above Examples, after regeneration by passing chlorobenzene through the bed, impure $\phi_2SiCl_2$ containing 780 PPM of biphenyls was fed through the bed at the same mass velocity used in Example 1, and the concentration of biphenyls in the effluent leaving the vessel monitored with the following results:

| Lbs. of Effluent $O_2SiCl_2$ per lb of absorbent in bed | PPM of Biphenyls in Total Effluent $O_2SiCl_2$ |
|---|---|
| 0.54 | 4 |
| 1.79 | 7 |
| 3.39 | 17 |
| 5.08 | 33 |
| 6.79 | 53 |
| 8.43 | 67 |
| 10.12 | 89 |
| 11.80 | 118 |
| 13.25 | 151 |

The following two Examples demonstrate the efficacy of using a "Push Solvent" which is weakly adsorbed relative to biphenyls, for displacing and recovering the $\phi_2SiCl_2$ left in the bed at the completion of adsorption steps (1) and (2) in the above description of the process.

EXAMPLE 5

To a bed of 347 grams of dry adsorbent (activated carbon, type Pittsburgh CAL, 12 × 40 mesh, manufactured by Calgon Corp.) packed in a one inch, schedule 40 steel pipe, four feet long, impure $\phi_2SiCl_2$ containing 4080 PPM of biphenyls was fed. When the effluent $\phi_2SiCl_2$ contained 3380 PPM of biphenyls, impure $\phi_2SiCl_2$ feed was stopped, and chlorobenzene was fed at a rate of 184 milliliters per hour. The concentrations of biphenyls and $\phi_2SiCl_2$ in the effluent from the bed while the chlorobenzene was being fed were monitored with the following results:

| % of $O_2SiCl_2$ Recovered from the bed | PPM of Biphenyls in Total $O_2SiCl_2$ Recovered |
|---|---|
| 42.4 | 4,490 |
| 61.1 | 4,640 |
| 81.2 | 5,930 |
| 93.9 | 10,100 |

EXAMPLE 6

To a bed of 347 grams of dry absorbent (activated carbon, type Pittsburgh CAL, 12 × 40 mesh, manufactured by Calgon Corp.) packed in a one inch, schedule 40 steel pipe, 4 feet long, the same impure $\phi_2SiCl_2$ used in Example 5 was fed. When the effluent $\phi_2SiCl_2$ contained 3150 PPM of biphenyls impure $\phi_2SiCl_2$ feed was stopped, and one liter of iso-octane was fed at a rate of 180 milliliters per hour. After completion of the feeding of iso-octane, chlorobenzene was then fed at the same rate. The concentration of biphenyls and $\phi_2SiCl_2$ in the effluent from the bed while the iso-octane was being fed were monitored with the following results:

| % of $O_2SiCl_2$ Recovered from the bed | PPM of Biphenyls in Total $O_2SiCl_2$ Recovered |
|---|---|
| 18.3 | 3,230 |
| 38.0 | 3,220 |
| 57.6 | 3,220 |
| 72.8 | 3,250 |
| 78.0 | 3,200 |
| 82.7 | 3,140 |
| 84.6 | 3,160 |
| 86.1 | 3,140 |
| 87.1 | 3,160 |
| 89.4 | 3,070 |
| 90.3 | 3,050 |
| 92.0 | 3,520 |
| 94.2 | 6,160 |

Comparison of the results of Examples 5 and 6 shows that the use of a solvent which is relatively weakly adsorbed by the bed, e.g. iso-octane as compared to a solvent which is more strongly adsorbed relative to the biphenyls, e.g. chlorobenzene, recovers the $\phi_2SiCl_2$ left in the bed at the end of adsorption in a purer form. Thus, less processing of the recovered $\phi_2SiCl_2$ L to further purify is required and an overall improvement in the yield of purified $\phi_2SiCl_2$ from the process realized. This is paticularly important if product of very high purity is desired since the capactiy of the bed, expressed as lbs of purfied product per lb of adsorbent, decreases as the specification on the purity of the product is lowered, and because of the lowered purity specification more regeneration and reprocessing per lb of purifed product is required. The increase in PPM of biphenyls in the recovered $\phi_2SiCl_2$ for the last two data points in the above table are due to the appearance of chlorobenzene in the effluent which is beginning the desorption of the biphenyls from the bed. The following two Examples demonstrate the efficacy of displacing the desorption solvent by feeding purified $\phi_2SiCl_2$ through the bed.

EXAMPLE 7

To a bed of 347 grams of adsorbent (activated carbon, type Pittsburgh CAL, 12 × 40 mesh, manufactured by Calgon Corp.) packed in a 1 inch, schedule 40 steel pipe, four feet long, which had been previously used for adsorption of biphenyls from impure $\phi_2SiCl_2$ and regenerated with chlorobenzene, impure $\phi_2SiCl_2$ containing 4080 PPM of biphenyls was fed at a rate of 94 milliliters per hour. The bed was filled with chlorobenzene at the start of the impure $\phi_2SiCl_2$ feeding. The concentration of biphenyls and $\phi_2SiCl_2$ in the effluent from the bed were monitored with the following results:

| Lbs. of Effluent $O_2SiCl_2$ per lb of absorbent in bed | PPM of Biphenyls in Total Effluent $O_2SiCl_2$ |
|---|---|
| 0.16 | 21 |
| 0.46 | 20 |
| 0.77 | 20 |
| 1.10 | 20 |
| 1.44 | 21 |
| 1.78 | 24 |
| 2.11 | 29 |
| 2.44 | 36 |
| 2.78 | 46 |

EXAMPLE 8

To a bed of 347 grams of adsorbent (activated carbon, type Pittsburgh CAL, 12 × 40 mesh, manufactured by Calgon Corp.) packed in a one inch, schedule 40 steel pipe, four feet long, which had been previously used for adsorption of biphenyls from impure $\phi_2SiCl_2$ and regenerated with chlorobenzene, two liters of purified $\phi_2SiCl_2$ containing three PPM of biphenyls was fed to displace the chlorobenzene from the bed. The same impure $\phi_2SiCl_2$ used in Example 7 was then fed at a rate of 94 milliliters per hour. The concentration of biphenyls and $\phi_2SiCl_2$ in the effluent from the bed were monitored with the following results for the effluent from the impure $\phi_2SiCl_2$ after it had passed through the bed.

| Lbs. of Effluent $O_2SiCl_2$ per lb of absorbent in bed | PPM of Biphenyls in Total Effluent $O_2SiCl_2$ |
|---|---|
| 0.30 | 0.4 |
| 0.50 | 0.8 |
| 0.78 | 2.7 |
| 1.05 | 5.6 |
| 1.31 | 11 |
| 1.55 | 17 |

-continued

| Lbs. of Effluent $\phi_2SiCl_2$ per lb of absorbent in bed | PPM of Biphenyls in Total Effluent $\phi_2SiCl_2$ |
|---|---|
| 1.82 | 24 |

Comparison of the results of Examples 7 and 8 shows that displacement of the desorption solvent, e.g. chlorobenzene with purified $\phi_2SiCl_2$ provides a product of improved purity when the adsorption step is resumed.

The following Example demonstrates the removal of biphenyls from $\phi_2SiCl_2$ by various adsorbents of different types.

EXAMPLE 9

Adsorbents listed below were each individually batch contacted with $\phi_2SiCl_2$ containing biphenyls in the concentrations shown by shaking for 24 hours and the concentration of biphenyls in the treated $\phi_2SiCl_2$ measured with the following results. In all experiments the weight ratio of untreated impure $\phi_2SiCl_2$ to dry adsorbent was four.

| Absorbent | PPM in $\phi_2SiCl_2$ Untreated | Treated |
|---|---|---|
| Activated Carbon, Pittsburgh BL, minus 325 mesh, manufactured by Calgon Corp. | 3100 740 | 87 27 |
| Activated Carbon, Pittsburgh CAL, 12 × 40 mesh, manufactured by Calgon Corp. | 3100 740 | 360 11 |
| Activated Coconut charcoal, Pittsburgh PCB, 4 × 10 mesh, manufactured by Calgon Corp. | 3100 740 | 1620 370 |
| Coconut Charcoal, 70 × 80 mesh Analabs, Inc. | 3100 740 | 530 360 |
| 10 × Molecular Sieves, 45 × 60 mesh, Hylar M, Guild Corp. | 740 | 360 |
| 13 × Molecular Sieves, 600 mesh, Davison Chemical Division, W.R. Grace and Co. | 740 | 180 |

I claim:

1. A process for removing biphenyls from impure silanes and siloxanes comprising (1) passing a first stream of impure silanes and siloxanes containing biphenyls into contact with an adsorbent bed selected from the class consisting of molecular sieves and charcoal and (2) adsorbing the biphenyls from said first stream of silanes and siloxanes on said adsorbent bed, and (3) removing a second stream of purified silanes and siloxanes from said adsorbent bed containing a smaller amount of biphenyls than said first stream.

2. The process of claim 1 wherein said first stream of silanes and siloxanes are passed into contact with said adsorbent bed until the silanes and siloxanes reach the desired purity and removing the second stream of the purified silanes and siloxanes from said adsorbent bed and then further comprising passing said first stream of impure silanes and siloxanes through said adsorbent bed until the adsorbent bed reaches a saturation point with respect to said biphenyls and removing partially purified silanes and siloxanes.

3. The process of claim 2 wherein said partially purified silanes and siloxanes are passed through additional adsorbent beds until the silanes and siloxanes reach the desired purity.

4. The process of claim 1 wherein after said adsorbent bed has reached the saturation point further comprising transmitting a push hydrocarbon solvent which is weakly adsorbed relative to said biphenyls to replace the purified silanes and siloxanes in said adsorbent bed.

5. The process of claim 4 further comprising passing into said adsorbent bed, a desorbent hydrocarbon solvent which is strongly adsorbent of said biphenyls relative to said adsorbent bed and which replaces said push hydrocarbon solvent in said adsorbent bed and recovering amount of said silanes and siloxanes from said push hydrocarbon solvent for further purification in an adsorbent bed.

6. The process of claim 1 comprising passing into said adsorbent bed, a desorbent hydrocarbon solvent which strongly adsorbs biphenyls from said adsorbent bed and which replaces the purified silanes and siloxanes in said adsorbent bed.

7. The process of claim 5, further comprising replacing said desorbent hydrocarbon solvent in said adsorbent bed with purified silanes and siloxanes and removing amounts of said silanes or siloxanes from said desorbent hydrocarbon solvent for further purification in an adsorbent bed.

8. The process of claim 7 further comprising removing said second stream of purified silanes and siloxanes from said adsorbent bed, collecting said silanes and siloxanes as purified product and passing said first stream of impure silanes and siloxanes through said adsorbent bed until said silanes or siloxanes reach the desired purity.

9. The process of claim 1 wherein the impure silanes and siloxanes are impure phenylchlorosilanes.

10. The process of claim 9 wherein said impure phenylchlorosilanes are diphenyldichlorosilanes.

11. The process of claim 1 wherein the process is carried out at ambient temperatures.

12. The process of claim 4 wherein said push hydrocarbon solvent is a saturated aliphatic hydrocarbon solvent of 4 to 16 carbon atoms.

13. The process of claim 12 wherein said push hydrocarbon solvent is iso-octane.

14. The process of claim 6 wherein said desorbent hydrocarbon solvent is selected from the class consisting of aromatic solvents, chlorinated aromatic solvents and chlorinated aliphatic solvents.

15. The process of claim 14 wherein said desorbent hydrocarbon solvent is chlorobenzene.

16. The process of claim 1 wherein said adsorbent bed comprises activated carbon of a size varying from 4000 mesh to one quarter of an inch.

17. The process of claim 1 wherein said silanes and siloxanes are fed through said adsorbent bed at a rate varying from 5 to 500 lbs. per hour, per square foot of the cross-section of the adsorbent bed.

18. The process of claim 1 further comprising transmitting inert gas through said adsorbent bed to remove said silane and siloxanes that fill the voids in said adsorbent bed and removing partially purified silanes and siloxanes for further purification.

19. The process of claim 18 further comprising heating said adsorbent bed to above 100° C for a sufficient time to remove the biphenyls and silanes and siloxanes adsorbed in said adsorbent bed with a stream of an inert gas and further purifying said impure silanes and siloxanes by passing through an adsorbent bed.

20. A process for removing biphenyls from impure silanes and siloxanes comprising (1) passing a first stream of impure silanes and siloxanes containing biphenyls into contact with an adsorbent bed selected from the class consisting of molecular sieves and charcoal; (2) adsorbing the biphenyls from said first stream on said adsorbent bed; (3) removing a second stream of purified silanes and siloxanes from said adsorbent bed containing a lesser amount of biphenyls than said first stream while said purified silanes and siloxanes do not exceed the desire purity; (4) continuing transmitting of said first stream of impure silanes and siloxanes through said adsorbent bed until said adsorbent bed reaches the saturation point with respect to the adsorption of said biphenyls; (5) adding a push hydrocarbon solvent to said adsorbent bed to displace and recover a quantity of silanes and siloxanes with a large quantity of biphenyls from said adsorbent bed for further purification; (6) passing a desorbent hydrocarbon solvent through said adsorbent bed to remove said push hydrocarbon solvent and removing a quantity of impure silanes and siloxanes containing large amounts of biphenyls from said push hydrocarbon solvent for further purification and said desorbent solvent adsorbing the biphenyls from the adsorbent bed (7) replacing said desorbent hydrocarbon solvent in said adsorbent bed with a quantity of purified silanes and siloxanes containing a small quantity of biphenyls (8) recovering said purified silanes and siloxanes containing a small quantity of biphenyls from said adsorbent bed; and (9) passing said first stream of impure silanes or siloxanes through said adsorbent bed and recovering said second stream of purified silanes and siloxanes containing a smaller quantity of biphenyls then said first stream therefrom.

* * * * *

UNITED STATES PATENT AND TRADEMARK OFFICE
CERTIFICATE OF CORRECTION

PATENT NO. : 4,127,598

DATED : November 28, 1978

INVENTOR(S) : Harry R. McEntee

It is certified that error appears in the above-identified patent and that said Letters Patent are hereby corrected as shown below:

Column 1, line 3, after 1977 delete ",now abandoned"

Column 1, line 25, after phenylchlorosilanes delete "."

Column 1, line 35, delete "silicon" and substitute therefore - silicone -

Column 2, line 63, delete "taining" and substitute therefore - tinuing -

Column 3, line 36, after the delete "adsorbent" and substitute therefore
- desorbent -

Column 3, line 39, after an delete "adsorbent' and substitute therefore
- desorbent -

Column 3, line 43, after the delete "adsorbent" and substitute therefore
- desorbent -

Column 3, line 46, after the delete "adsorbent" and substitute therefore
- desorbent -

Column 3, line 65, after the delete "adsorbent" and substitute therefore
-desorbent -

UNITED STATES PATENT AND TRADEMARK OFFICE
CERTIFICATE OF CORRECTION

PATENT NO. : 4,127,598
DATED : November 28, 1978
INVENTOR(S) : Harry R. McEntee

It is certified that error appears in the above-identified patent and that said Letters Patent are hereby corrected as shown below:

Column 4, line 17, after are delete "pased" and substitute therefore

- passed -

Column 6, line 19, after siloxanes delete "bu" and substitute therefore

- but -

Column 8, line 51, after of delete "adsorbent" and substitute therefore

- desorbent -

Column 8, line 55, after preferred delete "adsorbent" and substitute therefore - desorbent -

Column 8, line 57, after Other delete "adsorbent" and substitute therefore

- desorbent -

Column 8, line 67, after the delete "adsorbent" and substitute therefore

- desorbent -

Column 9, line 6, after the delete "adsorbent" and substitute therefore

- desorbent -

Column 9, line 12, delete "adsorbing" and substitute therefore - desorbing -

UNITED STATES PATENT AND TRADEMARK OFFICE
CERTIFICATE OF CORRECTION

PATENT NO. : 4,127,598
DATED : November 28, 1978
INVENTOR(S) : Harry R. McEntee

It is certified that error appears in the above-identified patent and that said Letters Patent are hereby corrected as shown below:

Column 9, line 13, after of delete "adsorbent" and substitute therefore

- desorbent -

Column 9, line 19, after the delete "adsorbent" and substitute therefore

- desorbent -

Column 9, line 21, after the delete "adsor-" and substitute therefore

- desor- -

Column 9, line 31, after the delete "adsor-" and substitute therefore

- desor- -

Column 14, line 6, after Effluent delete "$O_2SiCl_2$" and substitute therefore

- $\emptyset_2SiCl_2$ -

Column 14, line 7, after Effluent delete "$O_2SiCl_2$" and substitute therefore - $\emptyset_2SiCl_2$ -

Column 14, line 26, after Effluent delete "$O_2SiCl_2$" and substitute therefore - $\emptyset_2SiCl_2$ -

Column 14, line 27, after Effluent delete "$O_2SiCl_2$" and substitute therefore - $\emptyset_2SiCl_2$ -

UNITED STATES PATENT AND TRADEMARK OFFICE
CERTIFICATE OF CORRECTION

PATENT NO. : 4,127,598

DATED : November 28, 1978

INVENTOR(S) : Harry R. McEntee

It is certified that error appears in the above-identified patent and that said Letters Patent are hereby corrected as shown below:

Column 14, line 47, after Effluent delete "$O_2SiCl_2$" and substitute therefore $-\emptyset_2SiCl_2$ -

Column 14, line 48, after Effluent delete "$O_2SiCl_2$" and substitute therefore - $\emptyset_2SiCl_2$ -

Column 15, line 2, after Effluent delete "$O_2SiCl_2$" and substitute therefore - $\emptyset_2SiCl_2$ -

Column 15, line 3, after Effluent delete "$O_2SiCl_2$" and substitute therefore - $\emptyset_2SiCl_2$ -

Column 15, line 31, after of delete "$O_2SiCl_2$" and substitute therefore - $\emptyset_2SiCl_2$ -

Column 15, line 32, after Total delete "$O_2SiCl_2$" and substitute therefore - $\emptyset_2SiCl_2$ -

Column 15, line 53, after of delete "$O_2SiCl_2$" and substitute therefore - $\emptyset_2SiCl_2$ -

Column 15, line 54, after Total delete "$O_2SiCl_2$" and substitute therefore - $\emptyset_2SiCl_2$ -

UNITED STATES PATENT AND TRADEMARK OFFICE
CERTIFICATE OF CORRECTION

PATENT NO. : 4,127,598
DATED : November 28, 1978
INVENTOR(S) : Harry R. McEntee

It is certified that error appears in the above—identified patent and that said Letters Patent are hereby corrected as shown below:

Column 16, Line 4, after recovered delete "$\emptyset_2 SiCl_2$ L" and substitute therefore - $\emptyset_2 SiCl_2$ -

Column 16, Line 36, after Effluent delete "$O_2 SiCl_2$" and substitute therefore - $\emptyset_2 SiCl_2$ -

Column 16, Line 37, after Effluent delete "$O_2 SiCl_2$" and substitute therefore - $\emptyset_2 SiCl_2$ -

Column 16, Line 62, after Effluent delete "$O_2 SiCl_2$" and substitute therefore - $\emptyset_2 SiCl_2$"

Column 16, Line 63, after Effluent delete "$O_2 SiCl_2$" and substitute therefore - $\emptyset_2 SiCl_2$ -

Column 17, Line 2, after Effluent delete "$O_2 SiCl_2$" and substitute therefore - $\emptyset_2 SiCl_2$"

Column 17, Line 3, after Effluent delete "$O_2 SiCl_2$" and substitute therefore - $\emptyset_2 SiCl_2$ -

UNITED STATES PATENT AND TRADEMARK OFFICE
CERTIFICATE OF CORRECTION

PATENT NO. : 4,127,598
DATED : November 28, 1978
INVENTOR(S) : Harry R. McEntee

It is certified that error appears in the above-identified patent and that said Letters Patent are hereby corrected as shown below:

Column 17, Line 24, after in delete "$O_2SiCl_2$" and substitute therefore — $\emptyset_2SiCl_2$ —

Column 18, Line 9, after strongly delete "adsorbs" and substitute therefore — desorbs —

Signed and Sealed this

Fifteenth Day of April 1980

[SEAL]

Attest:

SIDNEY A. DIAMOND

Attesting Officer    Commissioner of Patents and Trademarks

REEXAMINATION CERTIFICATE (384th)

United States Patent [19]

McEntee

[11] B1 4,127,598

[45] Certificate Issued  Sep. 10, 1985

[54] PROCESS FOR REMOVING BIPHENYLS FROM CHLOROSILANES

[75] Inventor: Harry R. McEntee, Waterford, N.Y.

[73] Assignee: General Electric Co., N.Y.

Reexamination Request:
No. 90/000,667, Nov. 9, 1984

Reexamination Certificate for:
Patent No.: 4,127,598
Issued: Nov. 28, 1978
Appl. No.: 828,367
Filed: Aug. 29, 1977

Certificate of Correction issued Apr. 15, 1980.

Related U.S. Application Data

[63] Continuation-in-part of Ser. No. 770,329, Feb. 22, 1977, abandoned.

[51] Int. Cl.$^3$ ............................................. C07F 7/20
[52] U.S. Cl. ................................. 556/442; 556/450; 556/454; 556/456; 556/460; 556/461; 556/466
[58] Field of Search ............... 556/453, 454, 456, 450, 556/459, 466, 465, 442, 460, 461

[56] References Cited

U.S. PATENT DOCUMENTS

| | | | |
|---|---|---|---|
| 1,548,733 | 8/1925 | Moody . | |
| 2,340,898 | 2/1944 | Race | 174/14 |
| 2,395,491 | 0/1946 | Mavity | 260/674 |
| 2,405,853 | 8/1946 | Rosch | 210/203 |
| 2,416,504 | 2/1947 | Trautman et al. | 252/49.6 |
| 2,643,972 | 6/1953 | Weedman | 196/147 |
| 2,668,622 | 2/1954 | Irvine et al. | 210/113.5 |
| 2,831,008 | 4/1958 | Knopf | 260/448.2 |
| 2,985,706 | 5/1961 | Dobry | 174/14 |
| 3,223,642 | 12/1965 | Smith | 252/78 |
| 3,439,013 | 4/1969 | Delaval et al. | 260/448.2 |
| 3,483,306 | 12/1969 | Harper | 174/14 |
| 3,646,093 | 2/1972 | Puthet | 260/448.2 |
| 3,755,152 | 8/1973 | Gulick | 208/307 |
| 3,894,171 | 7/1975 | Kusay | 174/14 R |
| 4,026,917 | 5/1977 | Stalling et al. | 260/473 G |
| 4,042,498 | 8/1977 | Kennedy | 210/26 |
| 4,082,866 | 4/1978 | Link | 427/294 |
| 4,102,816 | 7/1978 | Stalling et al. | 252/428 |
| 4,110,344 | 8/1978 | Stalling et al. | 260/340.3 |
| 4,124,834 | 11/1978 | Walsh | 174/14 R |
| 4,156,689 | 5/1979 | Ashby et al. | 260/448.2 E |
| 4,353,798 | 10/1982 | Foss | 210/181 |

FOREIGN PATENT DOCUMENTS 496020  11/1938  United Kingdom .
361184  5/1973  U.S.S.R. .

OTHER PUBLICATIONS

Dow Corning Corp., "Retrofill of Transformers with Silicone Liquid", Statement Presented re "Public Hearing re: Use, Labeling and Disposal of Polychlorinated Biphenyl (PCBs) As Granted By the Toxic Substances Control Act, Section 6(e)", Jan. 24, 1977.

Dow Corning Corp., "Removal of PCB From Dow Corning (R) 561 Silicone Transformer Liquid by Charcoal Filtration."

Column Chromatographic Separation of Polychlorinated Biphenyls From Chlorinated Hydrocarbon Pesticides and Subsequent Gas Chromatographic Quantitation in Terms of Derivatives, Berg et al., Bulletin of Environmental Contamination and Toxicology, vol. 7, No. 6 at 338–347, 1972 (Berg et al. I).

Column Chromatographic Separation of Polychlorinated Biphenyls From Chlorinated Hydrocarbon Pesticides and Subsequent Gas Chromatographic Quantitation in Terms of Derivatives, Berg et al., Source and Date unknown (Berg et al. II).

Polychlorinated Biphenyls–In Aqueous Media–Extraction–Electron Capture Gas Chromatography, Dow Corning Corporate Test Method No. 0695 dated Feb. 25, 1976 (Dow Corning CTM 0695).

Polychlorinated Biphenyls–in Aqueous Media–Extraction–Electron Capture Gas Chromatography, Revised Dow Corning Corporate Test Method No. 0695 dated Nov., 1979 (Revised Dow Corning CTM 0695).

Polychlorinated Biphenyls–in Siloxane Fluids–Column Chromatography–Electron Capture Gas Chromatography, Dow Corning Corporate Test Method No. 0849 dated Apr. 23, 1976 (Dow Corning CTM 0849).

Polychlorinated Biphenyls–In Siloxane Fluids–Column Chromatography–Electron Capture Gas Chromatography, Revised Dow Corning Corporate Test Method No. 0849 dated Nov., 1979 (Revised Dow Corning CTM 0849).

Transcript of Jan. 24, 1977 Environmental Protection Agency Public Hearing On Use, Labeling and Disposal of Polychlorinated Biphenyls (PCB's) As Granted By The Toxic Substances Control Act, Section 6 (e) (EPA Transcript).

*Primary Examiner*—Paul F. Shaver

[57] ABSTRACT

A process for removing impurities such as biphenyls from impure silanes and siloxanes comprising contacting said impure silanes and siloxanes with an adsorbent bed selected from the class consisting of a molecular sieve bed and a charcoal bed such that said impurities are adsorbed on the bed and removing the purified silanes and siloxanes from said adsorbent.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-20 is confirmed.

New claims 21-28 are added and determined to be patentable.

*21. The process of claim 1 wherein silanes or siloxanes comprise the major constituent of the first stream.*

*22. The process of claim 21 wherein the first stream comprises at least about 2060 parts per million by weight of biphenyls.*

*23. The process of claim 21 wherein the first stream comprises at least about 3100 parts per million by weight of biphenyls.*

*24. The process of claim 23 wherein the difference between the amount of biphenyls in the first stream and the purified product is at least about 1480 parts per million by weight.*

*25. The process of claim 23 wherein the difference between the amount of biphenyls in the first stream and the purified product is at least about 2570 parts per million by weight.*

*26. The process of claim 21 wherein the biphenyls comprise polychlorinated biphenyls.*

*27. The process of claim 24 wherein the biphenyls comprise polychlorinated biphenyls.*

*28. The process of claim 25 wherein the biphenyls comprise polychlorinated biphenyls.*

* * * * *